(12) United States Patent
Emmel et al.

(10) Patent No.: US 7,982,046 B2
(45) Date of Patent: Jul. 19, 2011

(54) METHOD FOR THE PRODUCTION OF FUNCTIONALIZED FIVE-RING HETEROCYCLES, AND USE THEREOF

(75) Inventors: Ute Emmel, Frankfurt am Main (DE); Peter Rittmeyer, Sulzbach/Teunus (DE); Ulrich Wietelmann, Friedrichsdorf (DE)

(73) Assignee: Chemetall GmbH, Frankfurt am Main (DE)

( * ) Notice: Subject to any disclaimer, the term of this patent is extended or adjusted under 35 U.S.C. 154(b) by 658 days.

(21) Appl. No.: 12/083,411

(22) PCT Filed: Oct. 24, 2006

(86) PCT No.: PCT/EP2006/067731
§ 371 (c)(1),
(2), (4) Date: Jun. 13, 2008

(87) PCT Pub. No.: WO2007/048799
PCT Pub. Date: May 3, 2007

(65) Prior Publication Data
US 2009/0131685 A1    May 21, 2009

(30) Foreign Application Priority Data

Oct. 24, 2005 (DE) .......................... 10 2005 051 164

(51) Int. Cl.
*C07D 231/02* (2006.01)

(52) U.S. Cl. ...................................................... 548/110
(58) Field of Classification Search .................. 548/110
See application file for complete search history.

(56) References Cited

U.S. PATENT DOCUMENTS

| 6,509,474 B1 | 1/2003 | Lischka et al. |
| 7,208,614 B2 | 4/2007 | Meudt |

FOREIGN PATENT DOCUMENTS

| DE | 19849197 | 2/2000 |
| DE | 10150615 | 4/2003 |
| EP | 1 403 271 A1 | 3/2004 |

OTHER PUBLICATIONS

Huang, et al "Preparation of heteroarylboron compounds" (1999) Abstract 131:144631.
Parry, et al "5-Formyl-2-furylboronic acid as a versatile bifunctional reagent for the synthesis of pf.-extended heteroarylfuran systems", Organic & Biomolecular Chemistry. 1(a)1447-1449 (2003).
Li, et al. : "An Improved Protocol for the Preparation of 3-Pyridyl- and Some Arylboronic Acids", *J. Org. Chem.* 67 (2002), pp. 5394-5397.
Tomson, et al. "A General Synthesis of 5-Acrylnicotinates", *J. Org. Chem.* 49 (1984), pp. 5237-5243.

*Primary Examiner* — Taofiq A Solola
(74) *Attorney, Agent, or Firm* — Fulbright & Jaworski L.L.P.

(57) ABSTRACT

A method for producing functionalized CH-acidic five-ring heterocycles, the resultant five-ring heterocycles and the use thereof for producing pharmaceuticals and crop protection preparations.

39 Claims, No Drawings

METHOD FOR THE PRODUCTION OF FUNCTIONALIZED FIVE-RING HETEROCYCLES, AND USE THEREOF

This application is a §371 of PCT/EP2006/067731 filed Oct. 24, 2006, which claims priority from German Patent Application No. 10 2005 051 164.3 filed Oct. 24, 2005.

The present invention provides a process for producing functionalised CH-acidic five-membered-ring heterocycles, the five-membered-ring heterocycles that are obtainable by this process, and the use thereof for the production of pharmaceuticals and crop-protection preparations.

Many pharmaceutical active substances and agricultural chemicals contain the structural element of a five-membered-ring heterocycle. There are diverse synthesis strategies for the purpose of producing different five-membered-ring heterocycles; in addition to ring-constructing syntheses, so-called de novo syntheses, simple, commercially available five-membered-ring heterocycles may also be functionalised—that is to say, converted into more complex desired molecules—by conversions with metal-organic reagents, for example. For example, thiophene can be metalated in the 2-position with organolithium compounds (R—Li) and subsequently transformed with ethylene oxide into thiophene ethanol:

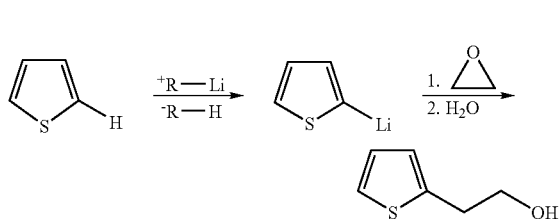

R = alkyl, aryl.

Thiophene ethanol is an important intermediate product in the production of thrombosis inhibitors such as ticlopidine or clopidogrel (Sanofi).

A disadvantage of this synthesis is constituted by the relatively high cost of the organolithium compounds. Moreover, the metalated intermediate products are very frequently thermally unstable—that is to say, they decompose or react in an undesirable manner with components of the reaction system. This applies, in particular, to reactions of the metalation reagent R—Li or of the lithiated intermediate stage with ethereal solvents—for example, cyclic ethers such as tetrahydrofuran (THF) or 2-methyltetrahydrofuran (MTHF). In consequence, metal-organic transformations of five-membered-ring heteroaromatics must, as a rule, be carried out at low temperatures—that is to say, at temperatures below −10° C., frequently even below −40° C.

Substantial progress for the purpose of improving economy has been able to be achieved through the replacement of organolithium compounds by the combination of lithium metal with a hydrogen acceptor (DE-C-198 49 197).

In the above case, cheap lithium metal serves as lithiation reagent, and the likewise added hydrogen acceptor—for example, an open-chain or cyclic 1,3-diene or a 1-arylolefin—prevents secondary reactions that have their origin in hydrogenation; for example:

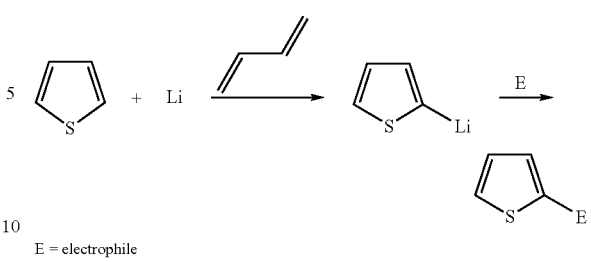

E = electrophile

However, a disadvantage of the above process is that the lithiated heterocycle is only insufficiently stable in ethereal solvents.

The metalated heterocycles that arise as intermediate stages are transformed by conversion with electrophiles into resultant products, for example boronic acids. In order to avoid undesirable by-products, this transformation is undertaken at very low temperatures. For instance, 2-furanboronic acid is prepared from 2-furyllithium and triisopropyl borate at −70° C. in THF (W. T. Thompson, J. Gaudino, J. Org. Chem. 1984, 49, 5237-5243):

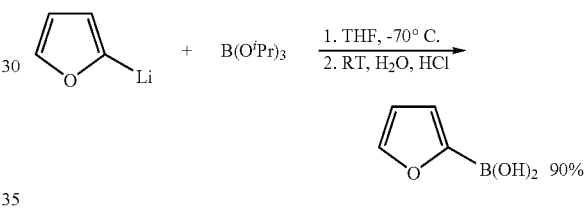

Moreover, it is possible to prepare the organolithium reagent that is used for the purpose of deprotonation—for example, butyllithium or cyclohexyllithium—in situ, and to carry out the lithiation reaction and also the reaction with an electrophile in a one-pot process (DE-A-101 50 615). For instance, 5-formylfuranboronic acid can be prepared as follows:

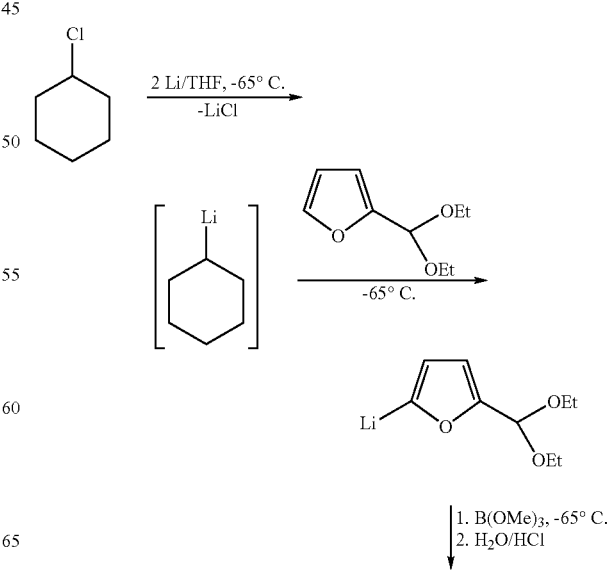

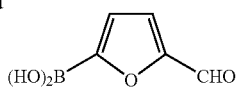

In this case the organolithium reagent—here, cyclohexyllithium—is produced in the presence of the substrate to be metalated—here, furfural diethyl acetal—and is converted after complete reaction with the electrophile—here, trimethyl borate. A disadvantage of this process is that lithium chloride (LiCl) is formed as a by-product of the synthesis, disrupting the processing. Moreover, the entire synthesis has to be conducted under cryogenic conditions around −65° C., which is correspondingly costly.

Moreover, it is known to produce boronic acids by so-called in-situ quench technology (in-situ quench: ISQ). To this end, the substrate—for example, a five-membered-ring heterocycle—is submitted in a mixture with the electrophile—as a rule, a boric acid ester—and a solvent—for example, THF—and the organometallic metalation agent are added. In this way, the lithiated intermediate reacts off directly with the electrophile—that is to say, undesirable secondary reactions cannot occur (W. Li, D. P. Nelson, M. S. Jensen, R. S. Hoerrner, D. Cai, R. D. Larsen, P. J. Reider, J. Org. Chem. 2002, 67, 5394-5397).

For example, 5-formylfuranboronic acid can be obtained in high purity in this way (EP-A-1 403 271):

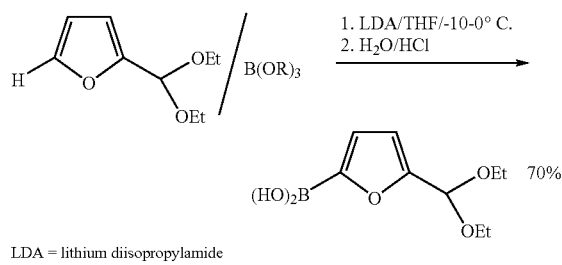

LDA = lithium diisopropylamide

A disadvantage of this method is that, although the synthesis has to be carried out at distinctly higher temperatures than the cryogenic temperatures ordinarily employed, it still has to be carried out at temperatures below 0° C. Moreover, an amine, in this case diisopropylamine, arises as by-product, which has to be separated off and disposed of.

It is therefore the object of the present invention to make available a process for producing functionalised five-membered-ring heterocycles that overcomes the disadvantages of the state of the art. In particular, the process is to permit CH-acidic five-membered-ring heterocycles to be derivatised in diverse manner by a metal-based technique.

In this connection:
the metalation reagent is to be readily available and inexpensive,
the process is to avoid unfavourable reaction conditions, in particular low temperatures,
the process is to provide the desired organic derivatisation product directly—that is to say, without formation or isolation of the metalated intermediate product,
the process is to be capable of being implemented easily in terms of apparatus—that is to say, it should be capable of being performed as a one-pot process.

In accordance with the invention the object is surprisingly achieved by virtue of the features of the main claim. Preferred configurations are to be found in the dependent claims.

In accordance with the invention the object is achieved by a process in which the combination of an alkali metal or a mixture of alkali metals, called 'alkali-metal component' for short in the following, and a hydrogen acceptor is taken as metalation reagent, and the metalation and derivatisation of the five-membered-ring heterocycle to be functionalised, called 'five-membered-ring substrate' for short in the following, with an electrophile are carried out entirely or partly under in-situ quench conditions. As distinct from the state of the art, the formation of the metalation-active species (the reaction intermediate arising from 1,3-diene or arylolefin and alkali-metal component) takes place in the presence both of the five-membered-ring substrate and of the electrophile. In this way a particularly high space-time yield can be obtained.

In accordance with the invention the alkali-metal component is preferably selected from one or more of lithium, sodium or potassium.

In accordance with the invention the five-membered-ring substrate is preferably selected from CH-acidic five-membered-ring heterocycles.

In accordance with the invention the hydrogen acceptor is preferably selected from one or more of open-chain or cyclic, non-substituted 1,3-dienes or 1,3-dienes substituted with alkyl or vinyl—for example, butadiene, isoprene or cyclohexadiene-1,3- or substituted or non-substituted 1-arylolefins—for example, styrene, methylstyrene or 1,1-diphenylethylene.

By way of electrophile, in accordance with the invention use may be made of all compounds that react with carbanionic substances. Carbon, boron and silicon electrophiles are preferably employed.

In accordance with the invention it is preferred to carry out the process according to the invention in the presence of one or more aprotic organic solvents.

In accordance with the invention the hydrogen acceptor is added in metered amounts to the alkali-metal component, or conversely. The remaining reactants—that is to say, the electrophile and the five-membered-ring substrate—are mixed before the start of the reaction either with the hydrogen acceptor or with the alkali-metal component. Similarly, in accordance with the invention it is possible to distribute the total quantity of the five-membered-ring substrate and of the electrophile in arbitrary proportions both onto the hydrogen acceptor and onto the alkali-metal component.

In accordance with the invention it is also possible to add to the reaction mixture partial quantities or the total quantity both of the electrophile and of the five-membered-ring substrate separately, but at least partly simultaneously with the uniting of the alkali-metal component and the hydrogen acceptor.

In one embodiment of the process according to the invention the alkali-metal component is submitted in an aprotic solvent, and the hydrogen acceptor, the five-membered-ring substrate and the electrophile are added in metered amounts, either separately or in a mixture.

In a further embodiment of the process according to the invention some or the total quantity of the five-membered-ring substrate and/or of the electrophile is submitted with the alkali-metal component in the solvent, and merely the hydrogen acceptor and also, as the case may be, the still lacking partial quantity of the five-membered-ring substrate and/or of the electrophile is/are added in metered amounts. However, this is only possible when the five-membered-ring substrate and/or the electrophile is/are sufficiently stable in relation to the alkali metal.

Should this not be the case or only insufficiently the case, at room temperature for example, a possibility that may present itself is to cool the submitted mixture of an alkali metal with the electrophile and/or with the five-membered-ring substrate, for example to 0° C. or lower.

In accordance with the invention it is also possible to submit a mixture consisting of five-membered-ring substrate, electrophile, hydrogen acceptor and, where appropriate, solvent, and to add the alkali metal in metered amounts with stirring.

In this case the alkali-metal component may be added in metered amounts in pure form—that is to say, in the form of dry solid or in the form of a melt. The molten form of addition comes into consideration, above all, for the low-melting alkali metals—for example, caesium (melting-point: 28.5° C.)—or alloys—for example, the Na/K alloy that is present in liquid form already at room temperature (RT).

A further metering option according to the invention consists in premixing the alkali-metal component in an inert solvent, where appropriate in a mixture with some or the total quantity of the five-membered-ring substrate and/or of the electrophile, and in adding the suspension, which has preferably been homogenised by stirring, in metered amounts to the likewise preferably stirred mixture of the lacking components—that is to say, to the hydrogen acceptor and, where appropriate, to the electrophile and/or, where appropriate, to the five-membered-ring substrate.

The process according to the invention will be elucidated on the basis of the example constituted by the production of boronic acid, without restricting the invention thereto. In the present case the electrophile is preferably boric acid ester.

It has surprisingly been found that alkali metals, in particular lithium and sodium, are sufficiently stable in relation to boric acid esters $B(OR)_3$, for example, that no undesirable direct reaction takes place, for example in accordance with:

Just as surprisingly, it has been found that boric acid esters also do not react with adducts consisting of the alkali-metal component and the hydrogen acceptor that are possibly formed as intermediates. Rather, it has been found that apparently only the metalated intermediate stage—here, the metalated five-membered-ring substrate—attacks the boric acid ester and forms the desired product, for instance furanboronic acid, with high yield. If, for example, use is made of lithium by way of metalation reagent, formyl furyl acetal by way of five-membered-ring substrate, and isoprene by way of hydrogen acceptor, then the reaction process can, for example, be illustrated as follows:

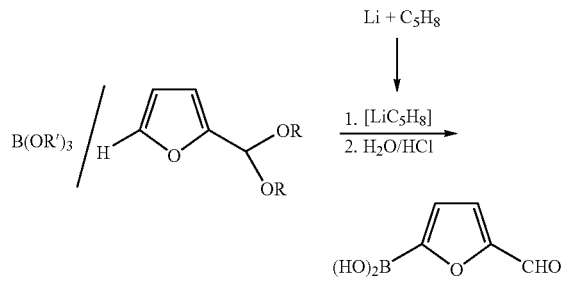

By way of five-membered-ring substrate, in accordance with the invention use is made of compounds that contain as ring members—in addition to at least one acidic CH grouping—a maximum of four heteroelements selected from one or more of oxygen (O), sulfur (S), nitrogen (N) and selenium (Se). The ring-carbon atoms may be present in unsubstituted form—that is to say, they may be bonded with only one or two hydrogen atoms—but they may also be bonded to other residues G.

Here and in the following, also in other contexts, the following apply, unless otherwise stated:

Residues denoted by R(R, R', $R^1$, etc.) are selected, independently of one another, from one or more of hydrogen (H), alkyl and/or aryl, preferably alkyl.

Residues denoted by G (G, G', $G^1$, etc.) are selected, independently of one another, from one or more of H, alkyl, aryl, Hal, perfluoroalkyl, perfluoroaryl. The alkyl or aryl residues may also contain one or more heteroatom-containing groups, the heteroatom being selected from one or more of O, N, P, S, Se, Si, Ge or B. The groups containing a further heteroatom are preferably those which contain one or more of the functions $-NR_2$, $-OR$,

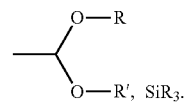

$SiR_3$.

Hal stands for halogen, preferably for fluorine and/or chlorine.

The five-membered-ring substrate contains at least one olefinic CH grouping in the α-position relative to a heteroatom. In this case the C-atom of the CH-acidic group is $sp^2$-hybridised.

The CH acidities of the five-membered-ring substrate exhibit a $pK_a$ value from 20 to 40. The following table lists some data. Benzene was chosen by way of reference example:

TABLE 1

CH acidities of selected five-membered-ring substrates

| Compound | Ring Heteroatom | $pK_a$ Values |
|---|---|---|
| Benzene (reference example) | ./. | 43 |
|  | X = S<br>X = O<br>X = N—R | 38.4 |
|  | X = S<br>X = O | 37.1<br>36.8 |
|  |  | 29.5 |
|  |  | 28.1 |

Suitable in particularly preferred manner are the following CH-acidic five-membered-ring heterocycles:

Five-membered-ring heterocycles with one heteroatom, such as, for example:

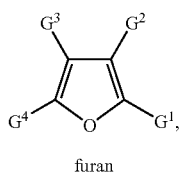
furan

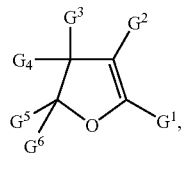
2,3-dihydrofuran

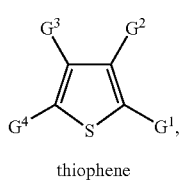
thiophene

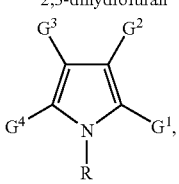
pyrrole

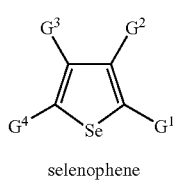
selenophene

Five-membered-ring heterocycles with two heteroatoms, such as, for example:

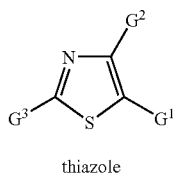
thiazole

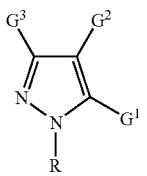
pyrazole

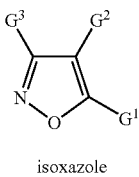
isoxazole

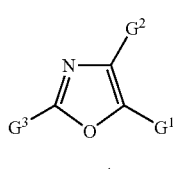
oxazole

Five-membered-ring heterocycles with three heteroatoms, such as, for example:

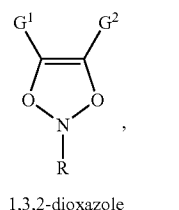
1,3,2-dioxazole

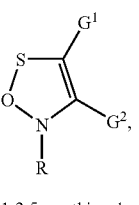
1,2,5-oxathiazole

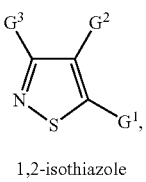
1,2-isothiazole

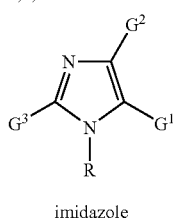
imidazole or five-membered-ring heterocycles with four heteroatoms, such as, for example:

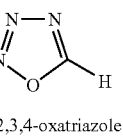
1,2,3,4-oxatriazole

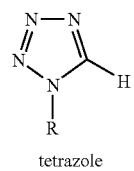
tetrazole at least one of the groups $G^1$ to $G^6$ being hydrogen, and this hydrogen being bonded to an $sp^2$-hybridised C-atom.

By way of suitable hydrogen acceptors, in accordance with the invention use is made of open-chain or cyclic, non-substituted 1,3-dienes or 1,3-dienes substituted with alkyl or vinyl, or substituted or non-substituted 1-arylolefins, preferably compounds having general structures listed in the following:

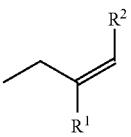

with $R^1$, $R^2$=H, alkyl, vinyl ($R^1$, $R^2$ in cis position or trans position),

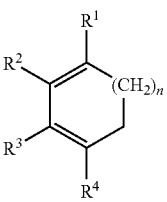

with n=1 to 5 and $R^1$, $R^2$, $R^3$, $R^4$=independently of one another, H or alkyl,

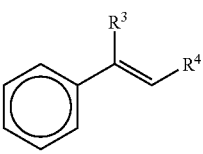

with $R^3$, $R^4$=H, alkyl ($R^3$, $R^4$ in cis position or trans position).

Particularly preferred are butadiene, isoprene cyclohexadiene-1,3, styrene, methylstyrene or 1,1-diphenylethylene.

It has been found that substituted or non-substituted 1-arylolefins—such as styrene, methylstyrene or 1,1-diphenylethylene—do not provide satisfactory results in all cases. The use of 1-arylolefins by way of hydrogen acceptors is restricted to the metalation of the relatively acidic five-membered-ring heterocycles—for example, thiazole or other multiply heterosubstituted five-membered rings. If 1-arylolefins are employed for the metalation of less acidic compounds—for example, thiophene or indole—the yields are distinctly poorer than with the use of 1,3-dienes.

If the alkali-metal component being used is not present in molten form, in accordance with the invention it is preferably present in finely divided form—that is to say, in the form of powder with particle sizes that are smaller than about 0.2 mm. In accordance with the invention, however, more lumpy forms—for example, granulated material with edge lengths of a few mm—can also be employed. Since the speed of reaction is dependent on the magnitude of the metal surface available, longer reaction times and/or poorer reaction yields are to be expected, as a rule, in the case where lumpy material is employed. In this case the alkali-metal component should be employed in distinct excess—that is to say, at least with 20% to 200% excess, preferably with at least 50% to 200% excess, relative to the amount of substance of the five-membered-ring substrate.

The alkali-metal-containing metalation reagent being used should exhibit as clean a metallic surface as possible—that is to say, a layer of corrosion products that is as little pronounced as possible. Corrosion products—such as, for example, alkali-metal oxides, carbonates, hydroxides or nitrides—inhibit the progress of the desired reaction, since they prevent the contact between alkali metal in oxidation state 0 and the reactants constituted by hydrogen acceptor, five-membered-ring substrate and electrophile. Therefore in accordance with the invention it is preferred to activate the metal by a process according to the state of the art, and/or to bring it into a physical form that is suitable for the metalation reaction only immediately prior to use.

For the purpose of activating the metal, metal phase-transfer catalysts, in the following called phase-transfer catalysts (PTC)— for example, naphthalene, anthracene, diphenyl or di-tert-butyldiphenyl, may be employed for example. In anhydrous polar-aprotic solvents the stated polycyclic aromatics are capable of adding alkali metals, with the formation of radical-anion complexes. As a result, the oxide layer on the metal is broken open, and the alkali metal is converted into a highly reactive soluble form. In this way the named catalysts diminish the undesirable induction phase; in addition, their presence in the reaction mixture has the result that less hydrogen acceptor is needed for the purpose of attaining a certain product yield. In accordance with the invention the PTC is added in concentrations from 0.0001 mol % to 5 mol %, preferably 0.001 mol % to 2 mol %, particularly preferably 0.01 mol % to 0.5 mol %, relative to the alkali-metal component employed.

In accordance with the invention a highly active alkali-metal component can also be generated by lumpy forms being melted down in the anhydrous solvent or solvent mixture being used under inert gas—for example, argon or nitrogen—and being dispersed in finely distributed form by means of a high-speed stirrer. Prior to implementation of the process according to the invention the charge is preferably cooled to the desired temperature, whereupon the alkali-metal component solidifies upon falling below the melting-point so as to form a highly reactive powder. This procedure is suitable, in particular, for sodium (melting-point: 98° C.) and potassium (melting-point: 64° C.). By way of electrophilic compounds, in principle all the compounds familiar to a person skilled in the art that react with carbanionic substances—in particular, carbon, boron and silicon electrophiles—may be employed. By way of boron electrophiles, use is preferably made of boric acid esters of the general formula $B(OR)_3$ or boron halides of the general formula $BHal_3$, particularly preferably trimethyl borate, triethyl borate, triisopropyl borate and tributyl borate.

By way of silicon electrophiles, use is made of compounds of the general formula $SiA_4$, wherein the substituents A stand, independently of one another, for the same or different $C_1$ to $C_6$ alkoxy, fluorine, chlorine, bromine, iodine, $C_1$ to $C_8$ alkyl or $C_6$ to $C_{20}$ aryl, but at least one of the substituents A is selected from the group comprising $C_1$ to $C_6$ alkoxy, fluorine, chlorine, bromine or iodine. Particularly preferred are dialkylsilicon halides and trialkylsilicon halides. Quite particularly preferred are trimethylchlorosilane and/or dimethyldichlorosilane.

By way of carbon electrophiles, in accordance with the invention use is made of:

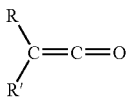

| | |
|---|---|
| epoxides: | $C_2H_4O$ or substituted derivatives |
| alkyl halides: | R-Hal |
| aryl halides: | Ar Hal |
| carbonyl compounds: | aldehydes, ketones, saturated or unsaturated |
| ketenes: | |
| nitriles: | aryl nitriles, hetaryl nitriles, or alkyl nitriles |
| amides: | R—CONR'$_2$ |
| carboxylic acids: | RCOOH, and also the alkali salts thereof |
| carboxylic esters: | RCOOR' |

With the process according to the invention, in each case at least 0.25 mol, and maximally 10 mol, of the alkali-metal component and also of the hydrogen acceptor and of the electrophile are employed per mole of the five-membered-ring substrate employed. In general, it is most sensible not to deviate too much from the ratios of theoretical stoichiometry—that is to say:

| | |
|---|---|
| five-membered-ring substrate: | 1 molar equivalent |
| alkali-metal component: | 1 molar equivalent |
| hydrogen acceptor: | between 0.5 molar equivalent and about 1 molar equivalent |
| electrophile: | 1 molar equivalent. |

However, in special cases it can make sense to employ, for example, the five-membered-ring heterocycle in excess: namely when it is cheap and the other components are to be utilised with yields that are as high as possible.

The stoichiometry of the hydrogen acceptor that is sensible in the individual case is dependent, above all, on the CH acidity of the five-membered-ring substrate. In the case of very acidic bonds ($pK_a$<about 30), as a rule half a molar equivalent is sufficient for a complete conversion. On the other hand, for relatively slightly acidic five-membered-ring substrates ($pK_a$>about 35—for example, furan, thiophene and such like) about one molar equivalent, in individual cases also more, has to be employed. It is generally preferred to employ at least 0.5 mol and at most 2 mol of the alkali-metal component and also of the hydrogen acceptor and of the electrophile per mole of the five-membered-ring substrate.

By way of solvent, in accordance with the invention aprotic organic compounds—such as ethers, hydrocarbons, tertiary amines or mixtures of these—are employed.

By way of ethers, open-chain or cyclic monoethers—for example, tetrahydrofuran (THF), 2-methyltetrahydrofuran (MTHF), tetrahydropyran (THP), diethyl ethers, dibutyl ethers, methyl tert-butyl ethers (MTBE)—or polyethers—for example, 1,2-dimethoxyethane (1,2-DME) or diethylene glycol dimethyl ether—are preferably employed, either in pure form or in a mixture with one another or in a mixture with ethers and/or hydrocarbons.

By way of hydrocarbons, pentane, hexane, cyclohexane, heptane, octane, methylcyclohexane, toluene, ethylbenzene or cumene, for example, are employed, either in pure form or in a mixture with one another or in a mixture with ethers and/or tertiary amines.

By way of tertiary amines, triethylamine, tributylamine, tetramethylethylenediamine (TMEDA), pyridine or similar, for example, are employed, either in pure form or in a mixture with one another or in a mixture with ethers and/or hydrocarbons.

Since hydrocarbons are generally distinctly less expensive than ethereal solvents, a high proportion of hydrocarbon in the solvent signifies an improved economic efficiency of the process according to the invention.

It is known that the reactivity of metal-organic compounds can be increased considerably by addition of strong donor solvents (Lewis bases), for example amines or ethers. Therefore the presence of strong donor solvents is preferred, particularly for the metalation of slightly reactive—that is to say, slightly acidic—five-membered-ring substrates by the process according to the invention.

In the course of the conversion according to the invention at least one hydrogen atom of the five-membered-ring substrate is exchanged for an alkali-metal atom. The hydrogen that is released in the process is accepted by the hydrogen acceptor. In the process, the singly hydrogenated monomer and/or the hydrodimerisation product is/are formed, and also, to a subordinate degree, higher oligomers of the hydrogenation product. With the use of isoprene, isopentene, for example, is formed, as well as a mixture consisting of dimethyloctadienes, and, moreover, very small quantities of unsaturated $C_{1-5}$ hydrocarbons.

Under reaction control according to the invention the alkali-metal salt of the five-membered-ring substrate which is formed in situ—that is to say, the metalated intermediate stage—reacts off immediately with the electrophile which is likewise present. As a result, depending on the precise reaction control the alkali-metal salt of the five-membered-ring substrate is present only in slight or even immeasurably small concentration. In this way the sometimes very reactive metalated intermediate stage is prevented from reacting in an undesirable manner with components of the reaction system, for example with the solvent.

The precise progress of the reaction is dependent on specific reaction parameters, for example on the reactivity of the metalated intermediate stage—that is to say, of the metalated five-membered-ring heterocycle, on the nucleophilicity of the electrophile, on the reaction temperature, and on the reaction control—that is to say, on the manner of metering of the electrophile. If the electrophile is present in stoichiometric quantity or in excess, it is to be assumed that the respective metalated intermediate stage is present in immeasurably small concentration at any time, because it reacts off immediately with the electrophile. Hence so-called ISQ conditions prevail. However, it is also possible to implement firstly the metalation reaction with a stoichiometric deficiency of the electrophile and to add the lacking quantity of electrophile only in delayed manner or after completion of the metalation reaction. In this case it may be necessary to work at distinctly lower temperatures than would be the case under total ISQ conditions.

In the sense of the process according to the invention the concentration of the electrophile in the reaction mixture amounts at any time to 10% to 500%, preferably 80% to 400%, particularly preferably 100% to 200%, of the concentration of five-membered-ring heterocycle added in metered amounts up until the same time.

In accordance with the invention the reaction temperatures lie between −80° C. and 100° C., preferably, however, within the range between −20° C. and 50° C. Depending on temperature and raw-material combination, in accordance with the invention the metering-times are between 20 minutes and 20 hours, preferably between one hour and 10 hours. After completion of the metering, a post-reaction phase follows which, in accordance with the invention, takes between 15 minutes and 2 hours.

After the end of the reaction the reaction mixture is processed in the usual manner. Any existing alkali-metal residues are frequently decomposed with water or with another protic compound, for example with alcohols, acids etc., and the desired organic compound is released. The isolation of the product is undertaken by filtration or distillation, for example. Frequently a number of extraction and/or phase-separation operations according to the state of the art precede these activities.

The functionalised five-membered-ring heterocycles isolated in this way find diverse use in organic chemistry, in particular for the production of pharmaceutical preparations and crop-protection preparations.

The subject-matter of the invention is, in detail:

- a process for producing functionalised five-membered-ring heterocycles by conversion of a five-membered-ring substrate with an electrophile, a hydrogen acceptor and an alkali-metal component, preferably in an organic solvent, wherein the formation of the metalated intermediate stage is undertaken in the presence of a five-membered-ring substrate and an electrophile;
- a process for producing functionalised five-membered-ring heterocycles by conversion of a five-membered-ring substrate with an electrophile, a hydrogen acceptor and an alkali-metal component, wherein the alkali component is submitted in an organic solvent, and the five-membered-ring substrate, the electrophile and the hydrogen acceptor are added in arbitrary sequence or simultaneously, as well as separately or in arbitrary mixtures;
- a process for producing functionalised five-membered-ring heterocycles by conversion of a five-membered-ring substrate with an electrophile, a hydrogen acceptor and an alkali-metal component, wherein the five-membered-ring substrate, the electrophile and the hydrogen acceptor are submitted in arbitrary sequence or simultaneously, as well as separately or in arbitrary mixtures, and the alkali-metal component is added, preferably suspended in an organic solvent;
- a process for producing functionalised five-membered-ring heterocycles, wherein a five-membered-ring substrate, an electrophile and a hydrogen acceptor are added in metered amounts, either in a mixture or separately, but simultaneously, to a suspension of an alkali-metal component in an organic solvent;
- a process for producing functionalised five-membered-ring heterocycles, wherein the hydrogen acceptor and the electrophile are added in metered amounts, either in a mixture or separately, but simultaneously, to the suspension of the alkali-metal component in a mixture consisting of an organic solvent and the five-membered-ring substrate;
- a process for producing functionalised five-membered-ring heterocycles, wherein the five-membered-ring substrate and the hydrogen acceptor are added in metered amounts, either in a mixture or separately, but simultaneously, to the suspension of the alkali-metal component in a mixture consisting of an organic solvent and the electrophile;

a process for producing functionalised five-membered-ring heterocycles, wherein the hydrogen acceptor is added in metered amounts to the suspension of the alkali-metal component in a mixture consisting of an organic solvent, the electrophile and also the five-membered-ring substrate;

a process for producing functionalised five-membered-ring heterocycles, wherein the suspension of the alkali-metal component in an organic solvent is added in metered amounts to a mixture consisting of the hydrogen acceptor, the electrophile and the five-membered-ring suspension and, where appropriate, an organic solvent;

a process for producing functionalised five-membered-ring heterocycles, wherein the suspension of the alkali-metal component in an organic solvent and also in the electrophile and/or in the five-membered-ring substrate is added in metered amounts to a mixture consisting of the hydrogen acceptor and/or the electrophile and/or the five-membered-ring substrate;

a process for producing functionalised five-membered-ring heterocycles, wherein the five-membered-ring substrate is a CH-acidic five-membered-ring heterocycle;

a process for producing functionalised five-membered-ring heterocycles, wherein the five-membered-ring substrate exhibits in the α-position relative to at least one ring heteroatom at least one CH-acidic group, the C-atom of which is $sp^2$-hybridised;

a process for producing functionalised five-membered-ring heterocycles, wherein the five-membered-ring substrate is selected from furan, 2,3-dihydrofuran, thiophene or pyrrole and this compound may be arbitrarily substituted, except for a CH-acidic group located in the α-position relative to the ring heteroatom;

a process for producing functionalised five-membered-ring heterocycles, wherein at least one CH-acidic bond of the five-membered-ring substrate exhibits a $pK_a$ value from 20 to 40;

a process for producing functionalised five-membered-ring heterocycles, wherein the hydrogen acceptor is selected from one or more of open-chain or cyclic, non-substituted 1,3-dienes or 1,3-dienes substituted with alkyl or vinyl, or substituted or non-substituted 1-arylolefins;

a process for producing functionalised five-membered-ring heterocycles, wherein the hydrogen acceptor is selected from one or more of butadiene, isoprene, cyclohexadiene-1,3, styrene, methylstyrene or 1,1-diphenylethylene;

a process for producing functionalised five-membered-ring heterocycles, wherein the alkali-metal component is selected from one or more of lithium, sodium, potassium;

a process for producing functionalised five-membered-ring heterocycles, wherein the alkali-metal component is employed in the form of powder or in the form of granulate;

a process for producing functionalised five-membered-ring heterocycles, wherein the alkali-metal component is dispersed in the solvent being used immediately prior to use;

a process for producing functionalised five-membered-ring heterocycles, wherein a compound that reacts with carbanionic substances is employed by way of electrophile;

a process for producing functionalised five-membered-ring heterocycles, wherein a carbon, boron and/or silicon electrophile is employed by way of electrophile;

a process for producing functionalised five-membered-ring heterocycles, wherein a boric acid ester of the general formula $B(OR)_3$ or boron halides of the general formula $BHal_3$, preferably trimethyl borate, triethyl borate, triisopropyl borate and tributyl borate, is employed by way of boron electrophile;

a process for producing functionalised five-membered-ring heterocycles, wherein a compound of the general formula $SiA_4$, preferably dialkylsilicon halides and trialkylsilicon halides, particularly preferably trimethylchlorosilane and/or dimethyldichlorosilane, is employed by way of silicon electrophile;

a process for producing functionalised five-membered-ring heterocycles, wherein the carbon electrophile is selected from one or more of epoxides, alkyl halides, aryl halides, carbonyl compounds, ketenes, nitriles, amides and/or carboxylic acids, the alkali salts and/or esters thereof;

a process for producing functionalised five-membered-ring heterocycles, wherein the electrophile concentration in the reaction mixture at any time amounts to 10% to 500%, preferably 80% to 400%, particularly preferably 100% to 200%, of the concentration of five-membered-ring heterocycle added in metered amounts up until the same time.

a process for producing functionalised five-membered-ring heterocycles, wherein an aprotic organic compound, preferably selected from hydrocarbons, ethers or tertiary amines, either in pure form or in a mixture, is employed by way of solvent;

a process for producing functionalised five-membered-ring heterocycles, wherein an open-chain or cyclic monoether or polyether, preferably THF, MTHF, THP, diethyl ether, dibutyl ether, MTBE, 1,2-DME and/or diethylene glycol dimethyl ether, either in pure form or in a mixture with one another or in a mixture with hydrocarbons, is employed by way of solvent;

a process for producing functionalised five-membered-ring heterocycles, wherein a tertiary amine, preferably triethylamine, tributylamine, tetramethylethylenediamine (TMEDA), pyridine, either in pure form or in a mixture with one another or in a mixture with ethers and/or hydrocarbons, is employed by way of solvent;

a process for producing functionalised five-membered-ring heterocycles, wherein a hydrocarbon, preferably an aliphatic or aromatic compound, particularly preferably pentane, hexane, cyclohexane, heptane, octane, methylcyclohexane, toluene, ethylbenzene or cumene, either in pure form or in a mixture with one another or in a mixture with ethers and/or tertiary amines, is employed by way of solvent;

a process for producing functionalised five-membered-ring heterocycles, wherein a phase-transfer catalyst (PTC) is added to the reaction mixture;

a process for producing functionalised five-membered-ring heterocycles, wherein the PTC is employed in concentrations from 0.0001 mol % to 5 mol %, preferably 0.001 mol % to 2 mol %, particularly preferably 0.01 mol % to 0.5 mol %, relative to alkali-metal component employed;

a process for producing functionalised five-membered-ring heterocycles, wherein between 0.25 mol and 10 mol, preferably between 0.5 mol and 2 mol, of the alkali-metal component, of the hydrogen acceptor and of the electrophile are employed per mole of the five-membered-ring substrate;

a process for producing functionalised five-membered-ring heterocycles, wherein the reaction temperatures are between −80° C. and 100° C., preferably between −20° C. and 50° C., particularly preferably between 0° C. and 40° C.;

a process for producing functionalised five-membered-ring heterocycles, wherein the metering-times are between 20 minutes and 20 hours, preferably between one hour and 10 hours;

a process for producing functionalised five-membered-ring heterocycles, wherein the post-reaction phase lasts for between 15 minutes and 2 hours;

a process for producing functionalised five-membered-ring heterocycles, wherein after complete conversion the reaction mixture is hydrolysed by aqueous/acidic means and the functionalised five-membered-ring heterocycle compound is isolated by one or more of the operations constituted by filtration, extraction or distillation;

functionalised five-membered-ring heterocycle, obtainable by the process according to the invention;

use of the functionalised five-membered-ring heterocycle produced by the process according to the invention for the purpose of producing pharmaceuticals and crop-protection preparations.

The invention will be elucidated on the basis of the following Examples, without restricting the invention thereto:

EXAMPLE 1

Production of 2-formylfuranboronic Acid from 2-furaldehyde Ethylene Acetal, Trimethyl Borate and Lithium Powder in THF In a thoroughly heated 250 ml Schlenk flask filled with argon 0.55 g (79 mmol) lithium powder (grain size<100 μm) in 120 g THF are submitted und magnetically stirred for 15 minutes at RT. Then a mixture consisting of 8.2 g (79 mmol) trimethyl borate, 5.1 g (75 mmol) isoprene und 10.5 g (75 mmol) 2-furaldehyde ethylene acetal is added dropwise within 200 minutes by means of an injection-metering device. In the process the internal temperature is maintained within the range between 25° C. and 30° C. by means of a water bath.

After completion of the dropwise addition, stirring is undertaken for a further 35 minutes at about 25° C. Then 50 ml water and 70 g 20% hydrochloric acid are added. Two liquid phases are formed, which are separated in a separating funnel. The aqueous phase is extracted three times with, each time, about 200 ml diethyl ether. The combined organic phases are twice shaken out with 50 ml water, dried with sodium sulphate and filtered. The filtrate is concentrated on a rotary evaporator. 167 g of concentrate are obtained.

In the concentrate a content of 2-formylfuranboronic acid of 6.1 wt. % is established by HPLC. This corresponds to a yield of 73 mmol or 97% of the theoretical value.

After total concentration by evaporation and recrystallisation of the solid residue consisting of acetonitrile/water (2:1), 9.2 g (66 mmol) of pure 2-formylfuranboronic acid are obtained.

EXAMPLE 2

Production of 2-formylfuranboronic Acid from 2-furaldehyde Diethyl Acetal, Trimethyl Borate and Lithium Granulate in THF In a thoroughly heated 250 ml Schlenk flask filled with argon 0.87 g (125 mmol) lithium-metal granulate (particles with 2 mm to 3 mm edge length) in 120 g THF are submitted. 12 mg biphenyl are added, and the charge is then stirred for about 30 min at RT. After this time the radical-anion complex consisting of lithium and biphenyl is formed, which imparts a greenish-brown colouring to the suspension.

Then a mixture consisting of 8.2 g trimethyl borate, 5.1 g isoprene and 12.8 g 2-furaldehyde diethyl acetal is added dropwise within three hours at internal temperatures between 22° C. and 25° C. After aqueous/acidic hydrolysis and processing as in Example 1, 190 g are obtained of an ethereal solution which contains 5.1% 2-formylfuranboronic acid. This corresponds to a yield of 92% of the theoretical value.

EXAMPLE 3

Production of 2-formylfuranboronic Acid from 2-furaldehyde Ethylene Acetal, Triisopropyl Borate und Lithium Powder in THF In a 250 ml Schlenk flask that had been rendered inert, 0.55 g lithium powder and 12 mg biphenyl are suspended in 8.5 g THF and stirred at RT. After a change in colour to greenish-brownish has taken place, firstly 20 g toluene are added and then the metered addition is begun of a mixture consisting of 8.2 g trimethyl borate, 5.3 g isoprene and 12.8 g 2-furaldehyde diethyl acetal. After the start of metering the internal temperature rises within 10 minutes from 23° C. to about 26° C. Then a further 55 g toluene are added, and the metered addition of the ternary mixture is continued. The mixture is added dropwise within 90 minutes.

After completion of the reaction, hydrolysis is undertaken by acidic means, and processing is undertaken as in Example 1.260 g are obtained of a yellowish solution which contains 3.3 wt. % 2-formylfuranboronic acid. This corresponds to a yield of 81% of the theoretical value.

EXAMPLE 4

Production of 2-formylfuranboronic Acid from 2-furaldehyde Ethylene Acetal, Triisopropyl Borate and Sodium Powder in THF In a 250 ml Schlenk flask that had been rendered inert, 1.81 g sodium powder (grain size<100 μm), 12 mg biphenyl and 120 g THF are submitted. After 15 minutes of stirring at RT a mixture consisting of 14.8 g triisopropyl borate, 5.1 g isoprene and 10.5 g 2-furaldehyde ethylene acetal is added dropwise within two hours at internal temperatures between 5° C. and 10° C., subject to water cooling.

After complete metered addition, stirring is undertaken for another hour at about 25° C., and the mixture is then poured into about 150 g of a stirred 15% hydrochloric acid that has been cooled to about 0° C. by means of ice.

After processing as described above, 260 g are obtained of a yellow-brownish solution which according to HPLC analysis contains 9.8 g 2-formylboronic acid. This corresponds to a yield of 93% of the theoretical value.

The invention claimed is:

1. A process comprising producing a functionalized five-member-ring heterocycle by converting a five-member-ring substrate with an electrophile, a hydrogen acceptor and an alkali-metal component, wherein at any time when the hydrogen acceptor with the alkali-metal component is jointly present in the charge the five-membered-ring substrate and the electrophile are also present in the charge, likewise in at least stoichiometric quantities relative to the hydrogen acceptor.

2. A process according to claim 1, wherein the alkali component is submitted in an organic solvent, and the five-membered-ring substrate, the electrophile and the hydrogen acceptor are added in arbitrary sequence or simultaneously, as well as separately or in arbitrary mixtures.

3. A process according to claim 1, wherein the five-member-ring substrate, the electrophile and the hydrogen acceptor are submitted in arbitrary sequence or simultaneously, as well as separately or in arbitrary mixtures, and the alkali-metal component is added, preferably suspended in an organic solvent.

4. A process according to claim 1, wherein a five-membering substrate, an electrophile and a hydrogen acceptor are added in metered amounts, either in a mixture or separately, but simultaneously, to a suspension of an alkali-metal component in an organic solvent.

5. A process according to claim 1, wherein the hydrogen acceptor and the electrophile are added in metered amounts, either in a mixture or separately, but simultaneously, to the suspension of the alkali-metal component in a mixture consisting of an organic solvent and the five-membered-ring substrate.

6. A process according to claim 1, wherein the five-member-ring substrate and the hydrogen acceptor are added in metered amounts, either in a mixture or separately, but simultaneously, to the suspension of the alkali-metal component in a mixture consisting of an organic solvent and the electrophile.

7. A process according to claim 1, wherein the hydrogen acceptor is added in metered amounts to the suspension of the alkali-metal component in a mixture consisting of an organic solvent, the electrophile and also the five-membered-ring substrate.

8. A process according to claim 1, wherein the suspension of the alkali-metal component in an organic solvent is added in metered amounts to a mixture consisting of the hydrogen acceptor, the electrophile and the five-membered-ring suspension and, where appropriate, an organic solvent.

9. A process according to claim 1, wherein the suspension of the alkali-metal component in an organic solvent and also in the electrophile or in the five-membered-ring substrate is added in metered amounts to a mixture consisting of the hydrogen acceptor or the electrophile or the five-member-ring substrate.

10. A process according to claim 1, wherein the five-member-ring substrate is a CH-acidic five-membered-ring heterocycle.

11. A process according to claim 1, wherein the five-member-ring substrate exhibits in the α-position relative to at least one ring heteroatom at least one CH-acidic group, the C-atom of which is $sp^2$-hybridized.

12. A process according to claim 1, wherein the five-member-ring substrate is selected from furan, 2,3-dihydrofuran, thiophene or pyrrole, and this compound may be arbitrarily substituted, except for a CH-acidic group located in the α-position relative to the ring heteroatom.

13. A process according to claim 1, wherein at least one CH-acidic bond of the five-membered-ring substrate exhibits a $pK_a$ value from 20 to 40.

14. A process according to claim 1, wherein the hydrogen acceptor is an open-chain or cyclic, non-substituted 1,3-diene, a 1,3-diene substituted with alkyl or vinyl, or a substituted or non-substituted 1-arylolefin.

15. A process according to claim 1, wherein the hydrogen acceptor is selected from butadiene, isoprene, cyclohexadiene-1,3, styrene, methylstyrene or 1,1-diphenylethylene.

16. A process according to claim 1, wherein the alkali-metal component is lithium, sodium or potassium.

17. A process according to claim 1, wherein the alkali-metal component is in the form of a powder or a granulate.

18. A process according to claim 1, wherein the alkali-metal component is dispersed in the solvent immediately prior to use.

19. A process according to claim 1, wherein the electrophile comprises a compound that reacts with a carbanionic substance.

20. A process according to claim 1, wherein the electrophile comprises carbon, boron or silicon.

21. A process according to claim 1, wherein the boron electrophile is a boric acid ester of the formula $B(OR)_3$ or a boron halide of the formula $BHal_3$.

22. A process according to claim 1, wherein the silicon electrophile is a compound of the formula $SiA_4$.

23. A process according to claim 1, wherein the carbon electrophile is an epoxide, an alkyl halide, an aryl halide, a carbonyl compound, a ketene, a nitrile, an amide, a carboxylic acid, or an alkali salt or ester thereof.

24. A process according to claim 1, wherein the electrophile concentration in the reaction mixture at any time amounts to 10% to 500% of the concentration of five-membered-ring heterocycle added in metered amounts up until the same time.

25. A process according to claim 1, wherein the organic solvent comprises an aprotic organic compound.

26. A process according to claim 1, wherein the solvent comprises an open-chain or cyclic monoether or a polyether.

27. A process according to claim 1, wherein the solvent comprises a tertiary amine.

28. A process according to claim 1, wherein the solvent comprises at least one hydrocarbon.

29. A process according to claim 1, further comprising adding a phase-transfer catalyst is added to the reaction mixture.

30. A process according to claim 1, wherein the phase-transfer catalyst is present in a concentration of from 0.0001 mol % to 5 mol % relative to alkali-metal component.

31. A process according to claim 1, wherein between 0.25 mol and 10 mol of the alkali-metal component, of the hydrogen acceptor and of the electrophiles are present per mole of the five-membered-ring substrate.

32. A process according to claim 1, wherein the reaction temperature is between −80 and 100° C.

33. A process according to claim 1, wherein the metering-time is between 20 minutes and 20 hours.

34. A process according to claim 1, wherein the post-reaction phase lasts for between 15 minutes and 2 hours.

35. A process according to claim 1, wherein after complete conversion the reaction mixture is hydrolyzed with an aqueous/acid and the functionalized five-membered-ring heterocyclic compound is isolated by the operations constituted by filtration, extraction or distillation.

36. A functionalized five-member-ring heterocycle, produced according to the process of claim 1.

37. A process comprising producing a pharmaceutical or crop-protection preparation by reacting the five-member-ring heterocycle prepared by the process of claim 1 to yield the pharmaceutical or crop-protection preparation.

38. A process according to claim 28, wherein the hydrocarbon is an aliphatic or aromatic compound.

39. A process according to claim 28, wherein the hydrocarbon is selected from the group consisting of pentane, hexane, cyclohexane, heptane, octane, methylcyclohexane, toluene, ethylbenzene or cumene.

* * * * *